(12) United States Patent
Maher

(10) Patent No.: US 6,694,636 B1
(45) Date of Patent: Feb. 24, 2004

(54) ELECTROCARDIOGRAM COMPASS

(76) Inventor: Kevin Maher, 1231 Split Rail Dr., Boothwyn, PA (US) 19061

( * ) Notice: Subject to any disclaimer, the term of this patent is extended or adjusted under 35 U.S.C. 154(b) by 0 days.

(21) Appl. No.: 09/943,337

(22) Filed: Aug. 30, 2001

Related U.S. Application Data

(60) Provisional application No. 60/229,920, filed on Sep. 1, 2000.

(51) Int. Cl.[7] .................................. G01B 3/16
(52) U.S. Cl. ........................ 33/807; 33/1 C; 33/1 SB
(58) Field of Search ................. 33/807, 1 C, 1 SB, 33/511, 512, 558.01, 558.04; 600/508, 509, 515, 516, 517, 518, 519, 520, 521, 522, 523

(56) References Cited

U.S. PATENT DOCUMENTS

| | | | |
|---|---|---|---|
| 297,492 A | | 4/1884 | Bovensiep |
| 3,129,514 A | | 4/1964 | Lintner |
| 3,358,371 A | | 12/1967 | Liesong, Sr. |
| 3,499,124 A | * | 3/1970 | Wortzman .................. 600/509 |
| 3,733,708 A | | 5/1973 | Goodman |
| 3,889,659 A | | 6/1975 | Lutes |
| 4,282,655 A | | 8/1981 | Tinman |
| 4,388,759 A | | 6/1983 | Orejola |
| 4,468,860 A | | 9/1984 | Rodengen |
| 4,504,832 A | | 3/1985 | Conte |
| 4,550,502 A | * | 11/1985 | Grayzel ....................... 33/1 C |
| 4,794,393 A | | 12/1988 | Imran |
| 5,056,238 A | | 10/1991 | Chi |
| 5,115,571 A | | 5/1992 | Mackin |
| 5,174,040 A | | 12/1992 | Grayzel |
| 5,430,954 A | | 7/1995 | Best et al. |
| 5,479,933 A | * | 1/1996 | Atarius et al. .............. 600/508 |
| 5,630,664 A | * | 5/1997 | Farrelly ....................... 600/508 |
| 5,875,561 A | | 3/1999 | Chen et al. |

FOREIGN PATENT DOCUMENTS

| | | |
|---|---|---|
| DE | 3400537 A1 | 7/1985 |
| GB | 2 155 407 A | 9/1985 |
| SE | 119 874 | 10/1947 |

* cited by examiner

*Primary Examiner*—G. Bradley Bennett

(57) ABSTRACT

The specification discloses a compass for obtaining measurements from an electrocardiogram tracing, the comprising a compass body, a display screen, compass legs pivotally connected to the body, and a computer operatively coupled to the display screen. The relative movement of the compass legs is translated into electronic signal information. The computer is adapted to receive the electronic signal information, and is further operative to convert the electronic signal information into physiological information to be displayed on the display screen. A power source powers the computer and display screen.

24 Claims, 2 Drawing Sheets

Fig. 2

|  | Mode I | Mode II | Mode III |
|---|---|---|---|
| Mode Function | Display time measurements | Display distance measurements | Calculate unknown |
|  | *Function Switch Functions in Mode* | *Function Switch Functions in Mode* | *Function Switch Functions in Mode* |
| Function Switch 15a | Change mode | Change mode | Change mode |
| Function Switch 15b | Convert time units | Convert distance units | Convert QTc value |
| Function Switch 15c | Change paper speed value | No function | Change paper speed value |
| Function Switch 15d | Display heart rate data | No function | Store measurements and effect calculation of unknown value |

ELECTROCARDIOGRAM COMPASS

RELATED APPLICATIONS

This application is related to, and claims the benefit of priority from, U.S. Provisional Patent Application Ser. No. 60/229,920, filed Sep. 1, 2000.

FIELD OF THE INVENTION

The present invention relates generally to tools for measuring electrocardiogram tracings and determining various physiological information therefrom.

BACKGROUND OF THE INVENTION

Electrocardiogram tracings are graphic representations of electromotive forces generated within the heart of a patient, which electromotive forces are transmitted across the chest wall and sensed by electrodes fixed to the patient's body. The standard electrocardiogram tracing displays these electromotive forces using Cartesian graphing, where the vertical axis represents the strength of the electromotive force, and the horizontal axis represents the duration of the electromotive force (i.e., the time during which the force is measured). From this graphical information a physician can determine numerous physiological data, including the patient's heart rate, axis deviations of the electrical axis of the heart, hypertrophy of chambers, conduction abnormalities, etc.

In most instances, electrocardiogram tracings are printed on graph paper comprising numerous minute boxes or squares. The common means of obtaining information from these tracings therefor consists of manually counting these boxes or squares, for instance with a common caliper or compass, a stylus, or other pointing implement. The measurements so obtained can then be input into known formulas for manual calculation of desired physiological data, including, for example, the $QT_c$ interval. However, this system is prone to inaccuracies and, thus, the production of flawed measurements and data.

Though the foregoing method is most commonly employed even today, prior art devices have attempted to overcome its inherent drawbacks. Orejola, U.S. Pat. No. 4,388,759, teaches an electrocardiogram caliper for reading electrocardiogram tracings. The caliper is entirely manual, operating much like a slide-rule; one arm of the caliper is calibrated for both amplitude in millivolts and duration of tracing deflections, while the other arm is calibrated for deflection frequency. Each arm further includes a predetermined index line for indexing against the calibrated scale on the opposite arm to thereby determine the values for the measurement made between the arms on the tracing. While an improvement over the unaided counting method described above, the Orejola device is still time-consuming to use, and suffers from an inability to provide more data by the physical limitations of space on the caliper.

A further electrocardiogram measuring device comprising a multi-legged caliper is disclosed in Grayzel, U.S. Pat. No. 5,174,040. That caliper includes a plurality of first parallel members pivotally connected to a plurality of second parallel members in a lattice-like arrangement. The first parallel members include points for aligning with cardiac events on the electrocardiogram tracing, while pivot points associated with the opposite ends of the parallel members are positionable along a predetermined scale calibrated to indicate various physiological data. Like the Orejola device, the Grayzel caliper suffers from an inability to provide more data by the physical limitations of space on the caliper, while its means of operation permits for providing no more than the most basic information from an electrocardiogram tracing.

A final device, taught in Imran, U.S. Pat. No. 4,794,393, comprises an electrocardiogram-tracing measuring device having first and second conductor-carrying members mounted for relative movement. A dielectric covering the conductors permits at least three capacitors to be formed in serial fashion upon relative movement of the first and second members. Electronics coupled to the capacitor translate this relative movement into information corresponding to the electrocardiogram tracing; specifically, milliseconds and beats-per-minute data. The Imran device unfortunately provides only the most fundamental data, and is further limited to measurements taken along the horizontal axis of the electrocardiogram tracing.

It would consequently be desirable to provide an electrocardiogram measuring device that overcomes the problems and disadvantages associated with the prior art.

SUMMARY OF THE DISCLOSURE

The present invention addresses and solves the problems discussed above, and encompass other features and advantages, by providing a compass for measuring parameters on an electrocardiogram tracing, and determining physiological information therefrom. The compass comprises a compass body, display screen, and compass legs pivotally connected to the compass body. Means are provided for translating relative movement of the compass legs into electronic signal information corresponding to the distance between the compass legs, which distance in turn corresponds to a measurement taken from an electrocardiogram tracing. The compass is further provided with a computer, for instance in the form of a microchip or the like, operatively coupled to the display screen and adapted to receive the electronic signal information, and further operative to convert the electronic signal information into one or more numerical values corresponding to physiological information to be displayed on the display screen. Thus, for example, a measurement of successive heartbeats is converted into beats-per-minute data, based upon known information such as paper speed and the distance units (e.g., millimeters) upon which the electrocardiogram-tracing measurement is taken. Distance in the horizontal plane is converted to information on the duration of an electromotive force (i.e., time), for measurement of intracardiac intervals. Distance in the vertical plane is converted to information on the duration of an electromotive force, reflective of voltage within the myocardium, and may, for example, be reported in millimeters. The compass is further adapted to calculate physiological information comprising at least one unknown value using one or more known formulas based upon one or more measurements taken with the compass, for instance the $QT_C$ interval value according to the known formula $QT_C = QT/\sqrt{R-R}$. To this end, the computer includes a memory for storing electronic signal information corresponding to one or more predetermined variables in one or more formulas for calculating physiological information from the electrocardiogram tracing. The computer is programmed with the one or more formulas, and is further operative to calculate the physiological data from the predetermined variables stored in the memory, and to display the physiological data on the display screen. According to a further feature of this invention, the computer may be provided with standard data for comparison with the calculated unknown value or values. For example, the computer may be provided with standard, or normal, $QT_C$ interval values for comparison with the calculated unknown $QT_C$ interval value.

A power source powers the computer, the computer memory, and the display screen.

BRIEF DESCRIPTION OF THE DRAWINGS

Other objects, features and advantages of the present invention will become apparent upon reference to the following description and drawings, in which:

FIG. 2 is a table representing the various modes and functions of the illustrated embodiment of the present invention.

DESCRIPTION OF THE ILLUSTRATED EMBODIMENT

Figure 1:
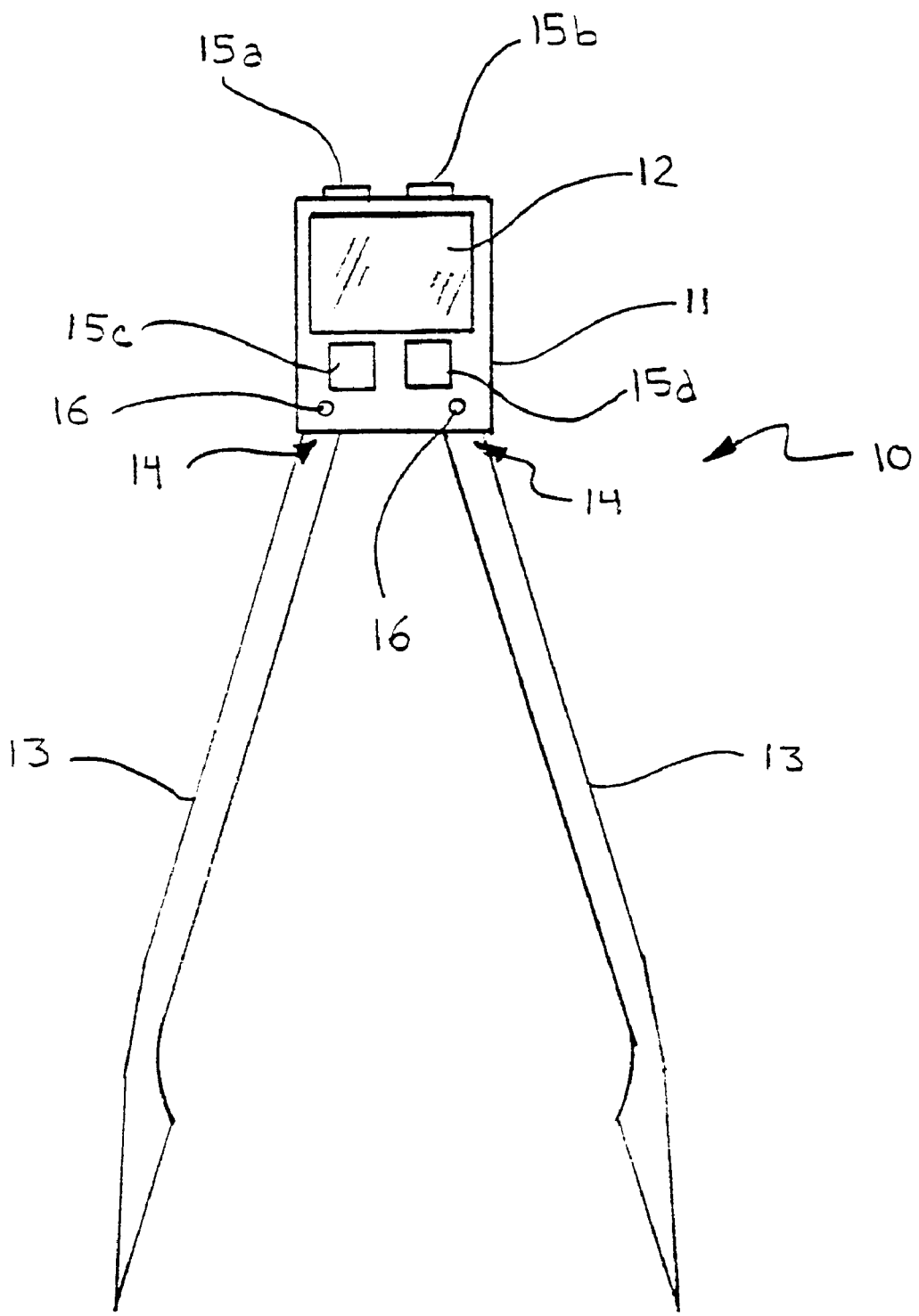
FIG. 1 depicts the present invention in elevation.

Referring now to the drawings, wherein like numerals indicate like or corresponding parts, the present invention will be seen to most generally comprise a compass 10 for measuring parameters on an electrocardiogram tracing (not shown) and providing visual display of a numerical value or values corresponding to physiological information derived from said measurements. The compass 10 comprises a compass body or housing 11 mounting a display screen 12 and compass legs 13 pivotally connected to the compass body 11 at first ends 14 thereof. (FIG. 1.) The display screen 12 comprises a low current electronic device for displaying numbers and/or letters as readouts, for instance a liquid crystal display (LCD) such as is known for use in conventional digital devices such as wristwatches. A computer (not shown), such as a logic circuit or microchip (or other electronics board of conventional manufacture), is provided in the compass body 11 and operatively connected to the display screen 12, for example by suitable wiring as is known to those of skill in the art. The computer preferably includes a memory for storing electronic signal information corresponding to one or more measurements taken between the compass legs 13, which measurement or measurements in turn correspond to one or more variables in one or more formulas programmed into the computer and used to determine physiological information from an electrocardiogram tracing, all as explained further herein. A suitable power source (not shown), such as a battery, is provided in circuit with the display screen 12, computer, and computer memory in order to power the same. Preferably, the body 11 includes a compartment accessible via a removable cover (not shown) for housing the power source. User-operable functional switches 15, such as pushbuttons, knobs, or comparable means, are provided, the switches 15 being operatively connected to the computer for the selection of various functions of the device with respect to the information obtained from the measuring portion thereof. The switches 15 may comprise resistors, such as shown and described in U.S. Pat. No. 4,468,860, issued to Rodengen, and the disclosure of which is incorporated by reference herein in its entirety. According to the illustrated embodiment, four such functional switches 15a–15d are provided, their operation being explained in greater detail below.

The compass legs 13 are pivotally secured to the compass body 11 by one or more bolts 16 extending through bores (not shown) provided through the first end 14 of each leg 13. In the illustrated embodiment, the compass legs 13 are secured to the compass body 11 at separate pivotal connections by separate bolts 16. However, a single, common pivotal connection between the legs 13 and compass body 11 may also be employed, the manner of connection not being limiting of the present invention.

Means are provided for translating relative movement of the compass legs 13 into electronic signal information corresponding to the distance between the compass legs 13, which electronic signal information is transmitted to the computer for the performance of one or more computational operations, whereupon desired physiological information relative to the electrocardiogram tracing is displayed on the display screen 12 in the form of numerical values, as further explained herein. These translating means may take any of a variety of forms, including a potentiometer (not shown) mounted between the compass legs 13 for determining the angular disposition therebetween, the potentiometer being provided in circuit with the computer and power source so that information from the potentiometer may be acted upon in the computer according to the function or functions selected by the compass user, all in the operational manner described hereinbelow. Such a potentiometer arrangement is described in U.S. Pat. No. 4,468,860, referenced above. Alternatively, an inductive rod apparatus may be employed, such as disclosed in U.S. Pat. No. 5,875,561, issued to Chen et al., the disclosure of which is incorporated by reference herein in its entirety. According to this means, not illustrated, an inductor rod is pivotally connected to the compass legs so as to be translationally positionable in response to relative movement of the legs. An inductor sleeve is provided in which the inductor rod slides with relative movement of the compass legs, translational movement of the inductor rod in the inductor sleeve sending a variable electronic pulse to the computer indicative of the relative position between the compass legs. By this variable electronic pulse, the computer computes the precise distance between the compass legs, and can further compute from this electronic pulse the heart rate charted on the electrocardiogram, as well as other physiological information, all as explained further below.

Referring now also to FIG. 2, the operation of the present invention will be better understood. The device is operative to take measurements along, and provide physiological information corresponding to, both horizontal and vertical axes of the electrocardiogram tracing, with measurements along the vertical axis corresponding to the strength of an electromotive force, measured by distance in millimeters or other units, and horizontal measurements corresponding to the duration of an electromotive force, measured in units of time such as milliseconds, seconds, etc., all in accordance with conventional electrocardiogram tracings.

The device preferably has a default, first operational mode, referred to as Mode I for purposes of distinction from the other modes discussed herein, being for example the display of measurement information taken from the horizontal axis (i.e., display information corresponding to the duration of an electromotive force). The display screen 12 will accordingly display the duration of an electromotive force in a given default unit of time, for instance milliseconds, and electronic signal information corresponding to the relative distance between the compass legs 13 from a given measurement will be converted by the computer into a corresponding period of time in the default unit according to the distance measured and the paper speed, and displayed on the display screen 12. The switch 15b is operative to direct the computer to conduct a conversion computation converting the default time unit to other time units, for instance seconds, minutes, or hours, and to vary the information provided on the display screen 12 accordingly. Formulae for converting between any number of different time units may be preprogrammed in the computer, variation between each conversion computation being selectable by depressing the switch 15b in Mode I. Likewise, paper speed, equating to distance traveled in a given time, may be varied by the switch 15c in like manner, each depression of the switch 15c resulting in the selection of one of any number of preprogrammed paper speeds employed by the computer in converting the measurement information obtained by the compass legs 13 into a time value. It is preferred that each change in the paper speed setting produce a corresponding readout change on the display screen 12 representing the paper speed being selected, to thereby confirm for the compass user the selection made.

One of the most common physiological measurements determined from electrocardiogram tracings is a patient's heart rate, which corresponds to the number of heart beats per unit of time. It is preferred that Mode I described above further include an information readout on the display screen 12 of heart rate as calculated by the computer using the time information calculated above for a measurement by the compass legs 13 between two points, in this case points representing successive heart beats, on the electrocardiogram tracing. This information may-be provided on the display screen 12 simultaneous with the display of time information discussed above, or may be displayed alternately according to an automatic cycle programmed into the computer. Alternatively, a switch 15d may select a readout displaying this heart rate information in Mode I. The latter is a preferred arrangement, since not every measurement taken by a user in Mode I will necessarily correspond to the distance between successive heart beats on the electrocardiogram tracing.

In the illustrated embodiment, the switch 15a is a mode selection button, and depressing that switch 15a will consequently vary both the computations performed by the computer in connection with any given measurement taken by the compass user, as well as the readout on the display screen 12.

In a further mode, Mode II, selected by the switch 15a, the device is operative to convert the electronic signal information corresponding to one or more measurements taken by the compass user along the vertical axis of the electrocardiogram tracing into information corresponding to the strength of an electromotive force, displayed as a distance value in millimeters or other units. As in Mode I, the display screen 12 will preferably display this distance value in a given default unit, for instance millimeters, and electronic signal information corresponding to the relative distance between the compass legs 13 will be converted by the computer into a corresponding distance measurement in millimeters. In this Mode II, the switch 15b is operative to cause the computer to conduct a conversion computation converting the default distance unit to other distance units, for instance centimeters or other metric units, or U.S. customary units, and to vary the information provided on the display screen 12 accordingly. Conversion formulae for any number of different distance units may be preprogrammed in the computer, variation between each conversion computation being selectable by depressing the switch 15b in Mode II.

In a further mode, Mode III, also selected by the mode-selection switch 15a, the device is operative to calculate physiological information corresponding to one or more unknown values using one or more a preprogrammed formulae requiring entry of one or more variables obtained by user-taken measurements between the compass legs 13. The memory is operative to store these variables measurements for subsequent input into the one or more preprogrammed formulae to compute the unknown value or values, which are then displayed on the display screen 12. In the illustrated embodiment, Mode III is selected to calculate a $QT_C$ interval from measurements obtained from the horizontal axis on the electrocardiogram tracing, using the known formula:

$$QT_C = QT/\sqrt{R\text{-}R}$$

There is preferably a default condition for Mode III, according to which all measurement information input into the computer, and subsequently displayed on the display screen 12, is in predetermined distance and time units, for instance millimeters and milliseconds, respectively. This default condition for Mode III preferably further includes a default paper speed setting. All of the default units and settings are preferably displayed on the display screen 12 when Mode III is selected. Upon selecting Mode III, the user may alter the paper speed setting in the manner described above by actuating the switch 15c. By subsequently actuating the switch 15d, the computer is programmed to provide a prompt on the display screen 12 requiring the user to make a measurement on the electrocardiogram tracing corresponding to one of the variables, for instance the QT interval, which compass measurement is converted by the computer into a corresponding time value and displayed on the display screen 12 to provide visual confirmation of the measurement. By actuating the switch 15d again, the displayed QT interval value is stored in the memory, and the user is again prompted to make a measurement on the electrocardiogram tracing, this time corresponding to the second variable, in this case the R-R interval, which measurement is converted by the computer into a corresponding time value and displayed on the display screen 12. Further actuating the switch 15d causes the computer to compute the unknown value $QT_C$ according to the known, preprogrammed formula using the above-entered and stored QT and R-R variables. The result of this computation is displayed on the display screen 12 in a default unit, for example seconds. In Mode III, the switch 15b is operative to cause the computer to convert the $QT_C$ result as displayed to other units for the variables, according to one or more preprogrammed conversion formulae. Preferably, the display screen 12 displays the converted variables from which the transposed $QT_C$ result is derived.

Depending upon the size of the memory employed in the present invention, it may also be desirable to input certain standard or normative EKG results so as to provide a reference for immediate comparison of results obtained with the present inventive compass. According to this embodiment of the invention, it may, for example, be desirable to provide standard $QT_C$ data to which the $QT_C$ result obtained as described above may be compared. Further to this embodiment, it would be preferable that the computer be operable to automatically compare the $QT_C$ result to preprogrammed standard or normative $QT_C$ data, and cause an abnormal $QT_C$ result to be specifically distinguished when displayed on the display screen 12, for example as a blinking display.

It will be appreciated from the foregoing that a variety of further modes may be provided, each capable of being selected via the single mode-selection switch 15a, including further modes operative to compute an unknown value or values from a preprogrammed formula or formulae, as in the manner discussed with respect to Mode III, for example.

Of course, it will be appreciated that the foregoing is merely illustrative of the present invention, and that additional modifications and improvements thereto, apparent to those of skill in the art, are possible without departing from the spirit and broader aspects of this invention as set forth in the appended claims.

What is claimed is:

1. A compass for obtaining measurements from an electrocardiogram tracing, comprising:

a display screen;

pivotally movable compass legs;

means for translating relative movement of said compass legs into electronic signal information corresponding to the distance between said compass legs;

a computer operatively coupled to said display screen, said computer adapted to receive said signal information, said computer being operative to convert said electronic signal information into one or more numerical values corresponding to physiological information to be displayed on said display screen, wherein said physiological information comprises at least one unknown value in one or more programmed formulas, said computer being operative to convert said electronic signal information into one or more numerical values corresponding to the variables in one or more programmed formulas and to calculate the at least one unknown value therefrom, and to display said calculated unknown value on said display screen, and wherein further said computer comprises a memory for storing said one or more numerical values corresponding to said one or more variables in said one or more programmed formulas; and a power source.

2. The electrocardiogram compass of claim 1, wherein said physiological information comprises heart rate information, said computer being operative to convert said electronic signal information into a numerical value corresponding to said heart rate information, and to display said numerical value corresponding to said heart rate information on said display screen.

3. The electrocardiogram compass of claim 2, further comprising a function switch for effecting both the conversion of said electronic signal information into said numerical value corresponding to said heart rate information, and the display of said numerical value corresponding to said heart rate information on said display screen.

4. The electrocardiogram compass of claim 1, wherein said physiological information comprises information on the duration of an electromotive force, said computer being operative to convert said electronic signal information into a numerical value corresponding to the duration of the electromotive force, and to display said numerical value corresponding to the duration of the electromotive force on said display screen.

5. The electrocardiogram compass of claim 4, wherein said computer is further operative to convert said numerical value corresponding to the duration of the electromotive force from a first unit of measurement into one or more further units of measurement, and to display said converted numerical value corresponding to the duration of the electromotive force on said display screen.

6. The electrocardiogram compass of claim 5, further comprising a function switch for effecting said conversion of said numerical value corresponding to the duration of the electromotive force into one or more further units of measurement.

7. The electrocardiogram compass of claim 1, wherein said physiological information comprises information on the strength of an electromotive force, said computer being operative to convert said electronic signal information into a numerical value corresponding to the strength of an electromotive force, and to display said numerical value corresponding to the strength of an electromotive force on said display screen.

8. The electrocardiogram compass of claim 7, wherein said computer is further operative to convert said numerical value corresponding to the strength of an electromotive force from a first unit of measurement into one or more further units of measurement, and to display said converted numerical value corresponding to the strength of an electromotive force on said display screen.

9. The electrocardiogram compass of claim 8, further comprising a function switch for effecting said conversion of said numerical value corresponding to the strength of an electromotive force into one or more further units of measurement.

10. The electrocardiogram compass of claim 1, wherein said one or more programmed formulas comprises the formula $QT_C = QT/\sqrt{R\text{-}R}$, said computer being operative to convert said electronic signal information into numerical values corresponding to the variables QT and R-R, to store said numerical values corresponding to the variables QT and R-R in said memory, and to calculate the unknown $QT_C$ interval value using said formula and said stored numerical values.

11. The electrocardiogram compass of claim 10, further comprising at least one function switch for effecting the storage of said numerical values corresponding to said variables QT and R-R in said memory, and for effecting input of said numerical values corresponding to said variables QT and R-R into said programmed formula.

12. The electrocardiogram compass of claim 1, wherein said computer includes standard data for comparison with said calculated unknown value.

13. The electrocardiogram compass of claim 10, wherein said computer includes standard $QT_C$ interval values for comparison with said calculated unknown $QT_C$ interval value.

14. A compass for obtaining measurements from an electrocardiogram tracing, comprising:

a display screen;

pivotally movable compass legs;

means for translating relative movement of said compass legs into electronic signal information corresponding to the distance between said compass legs;

a computer operatively coupled to said display screen, said computer adapted to receive said electronic signal information, and said computer having a memory;

a power source for powering said computer and said display screen;

wherein said electrocardiogram compass has a first mode of operation, according to which said computer is operative to convert said electronic signal information into a numerical value corresponding to the duration of an electromotive force, and to display said numerical value corresponding to the duration of an electromotive force on said display screen;

wherein said electrocardiogram compass has a second mode of operation, according to which said computer is operative to convert said electronic signal information into a numerical value corresponding to the strength of an electromotive force, and to display said numerical value corresponding to the strength of an electromotive force on said display screen;

wherein said electrocardiogram compass has a third mode of operation, according to which said computer is operative to convert said electronic signal information into one or more numerical values corresponding to one or more variables in one or more programmed formulas and to calculate at least one unknown value therefrom using said one or more programmed formulas, and to display said calculated unknown value on said display screen, and wherein further said one or more numerical values corresponding to said one or more variables in said one or more programmed formulas are stored in said memory; and at least one function switch for selecting between said first, second, and third modes of operation.

15. The electrocardiogram compass of claim 14, wherein, in said first mode of operation, said computer is operative to operative to convert said electronic signal information into a numerical value corresponding to heart rate information, and to display said numerical value corresponding to said heart rate information on said display screen.

16. The electrocardiogram compass of claim 15, further comprising a function switch for effecting both the conversion of said electronic signal information into said numerical value corresponding to said heart rate information, and the display of said numerical value corresponding to said heart rate information on said display screen.

17. The electrocardiogram compass of claim 14, wherein, in said first mode of operation, said computer is further operative to convert said numerical value corresponding to the duration of the electromotive force from a first unit of measurement into one or more further units of measurement, and to display said converted numerical value corresponding to the duration of the electromotive force on said display screen.

18. The electrocardiogram compass of claim 17, further comprising a function switch for effecting said conversion of said numerical value corresponding to the duration of the electromotive force into one or more further units of measurement.

19. The electrocardiogram compass of claim 14, wherein, in said second mode of operation, said computer is further operative to convert said numerical value corresponding to the strength of an electromotive force from a first unit of measurement into one or more further units of measurement, and to display said converted numerical value corresponding to the strength of an electromotive force on said display screen.

20. The electrocardiogram compass of claim 19, further comprising a function switch for effecting said conversion of said numerical value corresponding to the strength of an electromotive force into one or more further units of measurement.

21. The electrocardiogram compass of claim 14, wherein said one or more programmed formulas comprises the formula $QT_C = QT/\sqrt{R\text{-}R}$, said computer being operative to convert said electronic signal information into numerical values corresponding to the variables QT and R-R, to store said numerical values corresponding to the variables QT and R-R in said memory, and to calculate the unknown $QT_C$ interval value using said formula and said stored numerical values.

22. The electrocardiogram compass of claim 21, further comprising at least one function switch for effecting the storage of said numerical values corresponding to said variables QT and R-R in said memory, and for effecting input of said numerical values corresponding to said variables QT and R-R into said programmed formula.

23. The electrocardiogram compass of claim 14, wherein said computer includes standard data for comparison with said calculated unknown value.

24. The electrocardiogram compass of claim 21, wherein said computer includes standard $QT_C$ interval values for comparison with said calculated unknown $QT_C$ interval value.

* * * * *